United States Patent [19]

Effland et al.

[11] 4,166,119

[45] Aug. 28, 1979

[54] ANALGESIC AND TRANQUILIZING SPIRO[DIHYDROBENZOFURAN]PIPERIDINES AND PYRROLIDINES

[75] Inventors: Richard C. Effland, Bridgewater; Joseph T. Strupczewski, Flemington; Beth A. Gardner, Succasunna, all of N.J.

[73] Assignee: American Hoechst Corporation, Bridgewater, N.J.

[21] Appl. No.: 896,622

[22] Filed: Apr. 14, 1978

[51] Int. Cl.$^2$ .................. A61K 31/445; A61K 31/40; C07D 491/10

[52] U.S. Cl. .................. 424/267; 260/326.15; 260/326.34; 260/326.5 R; 260/326.5 CA; 424/274; 546/17; 546/216

[58] Field of Search .................. 260/293.58, 293.66, 260/326.13 H, 326.5 CA, 326.14 R, 326.34, 326.15; 424/267, 274; 546/17

[56] References Cited

U.S. PATENT DOCUMENTS

| | | | |
|---|---|---|---|
| 2,500,714 | 3/1950 | Spielman | 260/293.58 |
| 3,431,233 | 3/1969 | Murayama et al. | 260/293.58 |
| 3,649,635 | 3/1972 | von Strandtmann et al. | 260/326.14 |
| 3,962,259 | 6/1976 | Bauer et al. | 546/17 |

OTHER PUBLICATIONS

Chemical Abstracts, 44, 4907i (1950) [Kägi, H., et al., Helv. Chim. Acta, 32, 2489–2507 (1949)].

Primary Examiner—Alan L. Rotman
Assistant Examiner—Richard A. Schwartz
Attorney, Agent, or Firm—Curtis, Morris & Safford

[57] ABSTRACT

Novel Spiro[dihydrobenzofuran-piperidine and pyrrolidine]s and methods of preparing same are described. These compounds are useful as analgetics and tranquilizers and as intermediates.

23 Claims, No Drawings

ANALGESIC AND TRANQUILIZING SPIRO[DIHYDROBENZOFURAN]PIPERIDINES AND PYRROLIDINES

This invention relates to novel spiro[dihydrobenzofuranpiperidine and pyrrolidine]s, and the pharmaceutically acceptable acid addition salts thereof, which are useful as analgetics, tranquilizers and as intermediates therefor, to methods of preparing the same, to methods of treatment with pharmaceutically effective amounts thereof and to pharmaceutical compositions containing such compounds as essential active ingredients.

The compounds of the invention have the formula

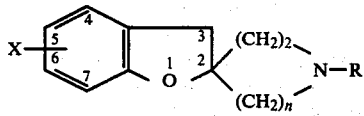

in which X is hydrogen, nitro, amino, chlorine, fluorine, bromine or methoxy; R is hydrogen, alkyl, alkenyl, hydroxyethyl, alkanoyl, alkoxyoxalyl, unsubstituted or substituted phenylalkanoyl, unsubstituted or substituted benzoyl, unsubstituted or substituted phenylalkyl, cycloalkylalkyl, cycloalkylcarbonyl, furfuryl, furoyl, alkoxycarbonyl, phenoxycarbonyl, unsubstituted or substituted phenoxyalkyl, N-[2-(3-indolylethyl] or (indol-3-yloxalyl); and n is 1 or 2.

Unless otherwise indicated, the terms "alkyl," "alkenyl," and "alkanoyl," whether used by themselves or in combination with other terms such as "phenyl" or "cycloalkyl," are intended to refer to such groups containing up to and including 6 carbon atoms; "cycloalkyl" means cycloalkyl of 3 to 7 carbon atoms, inclusive; and wherever the term "substituted" is used to modify "phenylalkanoyl," "benzoyl," "phenylalkyl," or "phenoxyalkyl," it is intended to refer to one or more nitro, amino, chlorine, fluorine, bromine or methoxy substituents.

Acids useful for preparing the pharmaceutically acceptable acid salts of the invention include inorganic acids such as hydrochloric, hydrobromic, sulfuric, nitric, phosphoric and perchloric acids, as well as organic acids such as tartaric, citric, acetic, succinic, maleic and fumaric.

To the best of our knowledge the compounds of the present invention have not heretofore been described or suggested. Spiro[phthalanpiperidine]s of the formula

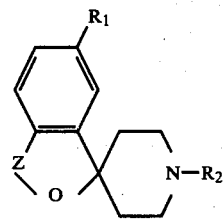

in which $R_1$ is hydrogen, loweralkyl, loweralkoxy, halogen or trifluoromethyl, $R_2$ is hydrogen or benzyl and Z is —$CH_2$— or —CO—, described by W. J. Houlihan et al. in U.S. Pat. No. 3,686,186, are outside the scope of this invention. The same applies to the natural product of the formula

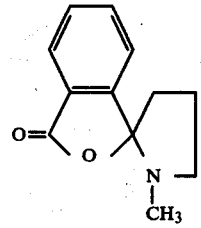

described by Y. Inubushi et al. [Chem. and Pharm. Bull (Japan) 12, 749 (1964)], as well as to substituted 1,3-dihydrospiro(isobenzofuran)s of the formula

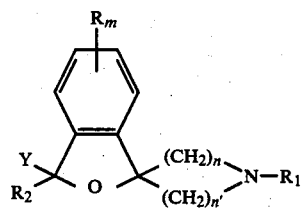

in which R is hydrogen, alkyl, alkoxy, trifluoromethyl, halogen, hydroxy or methylenedioxy; $R_1$ is hydrogen, alkyl, cycloalkylalkyl, alkenyl, phenylalkyl, diphenylalkyl, diphenylmethoxyalkyl, alkanoyl, phenylalkanoyl, benzoyl, benzoylalkyl, phenylhydroxyalkyl, alkoxycarbonyl, phenyloxycarbonyl or cycloalkylcarbonyl; $R_2$ is alkyl or phenyl; Y is hydrogen, alkyl, alkoxy, hydroxy or phenyl and m, n and n' are integers from 1 to 3; and to 1,3-dihydrospiro(isobenzofuran)s of the formula

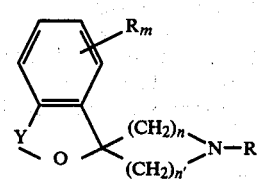

in which R is hydrogen, alkyl, alkoxy, trifluoromethyl, halogen, hydroxy or methylenedioxy; $R_1$ is alkyl, cycloalkylalkyl, phenylalkyl, diphenylalkyl, diphenylmethoxyalkyl, alkanoyl, phenylalkanoyl, benzoylalkyl, phenylhydroxyalkyl or cycloalkylcarbonyl; Y is $CH_2$ or CO; m is 1 or 2 and n and n' are integers from 1 to 3, described by Victor J. Bauer and Raymond W. Kosley, Jr. in U.S. Pat. Nos. 3,959,475 and 3,962,259, respectively.

The compounds of the invention are prepared by the sequence of reactions described below. In this description, the definitions of X, R and n are as defined earlier unless noted to the contrary.

A 2-fluorobenzyl chloride or bromide of the formula

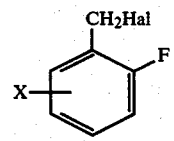

in which Hal is chlorine or bromine is converted to its Grignard reagent, preferably by use of ether as a solvent and a crystal of iodine to initiate the reaction. The Grignard reagent is reacted with a cycloazalkanone of the formula

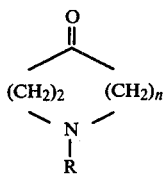

in which R can be alkyl, alkenyl, cycloalkylalkyl or phenylalkyl to provide immediate precursors of the formula

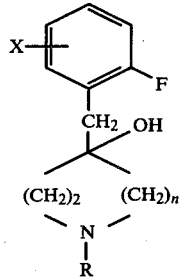

to compounds of the invention. "Fluorocompounds Related to the Reversed Esters of Pethidine," by N. J. Harper and A. B. Simonds, Journal of Medicinal and Pharmaceutical Chemistry, Vol. 1, No. 2 (1959) describes compounds falling within this class of precursors.

These precursors are reacted with a non-nucleophilic base in the presence of a solvent at a temperature of from 25° C. to the reflux point of the solvent to provide compounds of the invention, an N-substituted spiro[dihydrobenzofuran-piperidine]s or an N-substituted spiro[dihydrobenzofuran-pyrrolidine]s, of the formula

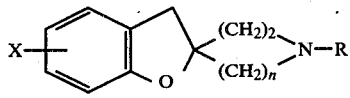

in which R is alkyl, alkenyl, cycloalkylalkyl or phenylalkyl. In a preferred embodiment, sodium hydride is used as the base, dimethylformamide and benzene are used as a combined solvent and the temperature is the reflux temperature.

An N-benzyl compound of the invention (R is benzyl) so prepared can be hydrogenated by any convenient method to provide the corresponding N-unsubstituted compound of the invention (R=H). A preferred method involves hydrogenation with a palladium on carbon catalyst.

An alternative method for preparing the N-unsubstituted compounds of the invention involves treating an N-substituted compound of the invention in which R is alkyl, alkenyl, cycloalkylalkyl or phenylalkyl with a chloroformate, e.g., an alkylchloroformate or phenylchloroformate, at a temperature of 25°–125° C., in a solvent such as toluene or benzene to provide the corresponding N-alkoxycarbonyl or N-phenoxycarbonyl compound of the invention (R=CO$_2$ alkyl or CO$_2$-phenyl). This in turn can be treated with a base such as sodium or potassium hydroxide in a solvent such as water or ethanol, or with an acid such as hydrogen bromide in acetic acid under reflux conditions, to provide the corresponding N-unsubstituted compound of the invention (R=H).

An N-unsubstituted compound of the invention can be reacted in a known fashion with an alkanoyl halide or anhydride, cycloalkylcarbonyl halide, phenylalkanoyl halide, benzoyl halide, or anhydride, furoyl halide or anhydride, or ethyloxalyl halide to provide the corresponding N-substituted compound of the invention in which the N-substituent (R) is alkanoyl, cycloalkylcarbonyl, phenylalkanoyl, benzoyl, furoyl or ethyloxalyl. A solvent such as pyridine or chloroform is used in this reaction. The use of an acid scavenger such as sodium bicarbonate, potassium carbonate or triethylamine is optional. The reaction temperature can vary from about 0° C. to the reflux point of the solvent. Reflux conditions usually enhance the rate of the reaction.

An N-substituted compound thus prepared can be reduced to provide the corresponding compound of the invention in which the N-substituent (R) is alkyl, cycloalkylalkyl, phenylalkyl or furfuryl. Preferred reducing agents utilized in this reducing step are diborane, lithium aluminum hydride or sodium bis(2-methoxyethoxy)aluminum hydride (VITRIDE ®) in a solvent such as tetrahydrofuran or benzene.

Similarly, an N-alkoxyoxalyl compound of the invention, prepared as described previously, can be reduced to provide the corresponding compound in which R is hydroxyethyl.

An N-unsubstituted compound of the invention can be reacted with a compound depicted by the formula R-Y in which R is alkyl, alkenyl, phenylalkyl, furfuryl, indol-3-yloxalyl or

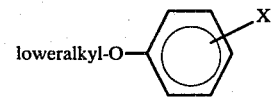

and Y is a halogen, preferably chlorine or bromine, to provide the corresponding N-substituted compound of the invention in which R is as indicated immediately above. In this procedure the reaction occurs in a solvent, such as isopropyl alcohol or dimethylformamide, at a temperature ranging from about ambient to reflux of the reaction mixture. Optionally an acid scavenger such as potassium carbonate or triethylamine and a reaction initiator such as potassium iodide may be employed.

An N-(indol-3-ylglyoxyloyl) compound, prepared in this manner, is reduced using lithium aluminum hydride in the manner described previously to provide the corresponding N-[2-(3-indolyl)ethyl] compound of the invention, in which R is

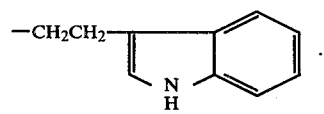

A compound of the invention in which X is hydrogen and R is alkyl or alkanoyl, prepared by any of the above methods, can be treated with a mixture of concentrated nitric acid in glacial acetic acid to provide the corresponding compound of the invention in which the 5-position of the ring structure contains a nitro substituent. This reaction is carried out at a temperature ranging from 25° to 150° C., preferably 100° C.

A compound of the invention in which R is alkanoyl can be subjected to hydrolysis to prepare the corresponding N-unsubstituted compound of the invention (R=H), e.g., by treatment with a strong acid such as 6 N hydrochloric acid at reflux conditions.

A compound of the invention in which X is $NO_2$ can be subjected to catalytic reduction to provide the corresponding compound of the invention in which X is amino. One such method involves hydrogenation under high pressure with a Raney nickel catalyst.

The compounds of the present invention are useful as analgetics due to their ability to alleviate pain in mammals. This analgetic utility of compounds of this invention is demonstrated in the phenyl-2-quinone writhing assay in mice, a standard assay for analgesia [Proc. Soc. Exptl. Biol. Med., 95, 729 (1957)]. Tabulated below are the percentages of inhibition of writhing accomplished with various subcutaneous dosages of representative compounds of the invention.

| Compound | Dose mg/kg | % Inhibition |
|---|---|---|
| 2,3-dihydro-1'-methylspiro-[benzofuran-2,4'-piperidine]-hydrochloride | 10 | 38 |
| 2,3-dihydro-1'-cyclobutylmethyl-spiro[benzofuran-2,4'-piperidine]-hydrochloride | 1.6 | 50 |
| 2,3-dihydro-1'-(β-phenethyl)spiro-[benzofuran-2,4'-piperidine]-hydrochloride | 3.3 | 50 |
| 2,3-dihydro-1'-(β-phenethyl)spiro-[benzofuran-2,3'-pyrrolidine]oxalate | 9.2 | 50 |
| 2,3-dihydro-5-nitrospiro[benzofuran-2,4'-piperidine]hydrochloride | 1.0 | 68 |

For comparison, aspirin and propoxyphene, known analgesic agents, effect a 34% and 50% inhibition at a dose of 60 mg/kg and 28 mg/kg, respectively. These data illustrate that the compounds of this invention are useful for alleviating pain in mammals when administered in amounts ranging from 0.05 to about 100 mg per kg of body weight per day.

Compounds of the present invention are also considered useful as tranquilizers due to their depressant action on the central nervous system of mammals. Compounds are useful as tranquilizers when administered in amounts ranging from 0.05 to 100 mg/kg per day.

Other compounds of the invention include:
2,3-dihydro-5-aminospiro[benzofuran-2,4'-piperidine];
2,3-dihydro-1'-cyclohexylmethylspiro[benzofuran-2,4'-piperidine];
2,3-dihydro-5-methoxyspiro[benzofuran-2,4'-piperidine];
2,3-dihydro-5-methoxyspiro[benzofuran-2,3'-pyrrolidine];
2,3-dihydro-5-fluoro-1'-n-propylspiro[benzofuran-2,4'-piperidine];
2,3-dihydro-6-methoxyspiro[benzofuran-2,3'-pyrrolidine];
2,3-dihydro-1'-ethylspiro[benzofuran-2,3'-pyrrolidine];
2,3-dihydro-1'-(trimethoxybenzoyl)spiro[benzofuran-2,3'-pyrrolidine];
2,3-dihydro-6-bromospiro[benzofuran-2,3'-pyrrolidine];
2,3-dihydro-1'-benzoylspiro[benzofuran-2,4'-piperidine];
2,3-dihydro-7-nitrospiro[benzofuran-2,4'-piperidine];
2,3-dihydro-4-chlorospiro[benzofuran-2,4'-piperidine]; and
2,3-dihydro-1'-phenoxycarbonylspiro[benzofuran-2,4'-piperidine].

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, exlixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a distintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied to between 0.5% and about 30% of the weight thereof. The amount of active compound in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The present invention is further illustrated by the following examples of representative compounds and procedures:

EXAMPLE 1

A. A few millileters of 2-fluorobenzyl chloride (from a solution of 14.5 g of 2-fluorobenzyl chloride in 75 ml of ether) are added to a mixture of 2.7 g of magnesium shavings in 25 ml of ether containing a crystal of iodine. The reaction is initiated by warming gently with a hot air gun. After the reaction begins, the remainder of the 2-fluorobenzyl chloride solution is added dropwise while maintaining the reaction mixture at reflux. After total addition, the reaction mixture is stirred at reflux for an additional 15 minutes before adding dropwise with vigorous stirring a solution of N-benzyl-4-piperidone in 75 ml of ether. The resulting suspension is stirred at ambient temperature for about 2 hours and then filtered. The filter cake is washed thoroughly with ether before being hydrolyzed by stirring with an ammonium chloride solution. The aqueous mixture is extracted with ether, the combined ether extracts are dried and then the ether is removed, leaving a yellow green oil. The oil is purified by distillation, leaving a yellow oil which solidifies upon standing to the light yellow solid, 1-benzyl-4-(2-fluorobenzyl)-4-piperidinol.

B. A solution of 6.9 g of 1-benzyl-4-(2-fluorobenzyl)-4-piperidinol in 25 ml of dimethylformamide and 10 ml of benzene. is added to a stirred suspension of 1.4 g of 50% sodium hydride in 50 ml of dimethylformamide and 10 ml of benzene. The mixture is heated at 110°-120° C. for 5 hours with an air condenser to allow evaporation of the benzene. Thereafter, the mixture is permitted to cool to ambient temperature. The cooled mixture is poured over ice, diluted with water and then extracted with ether. The ether phase is washed successively with water and a saturated sodium chloride aqueous solution and then dried. The ether is removed from the dried solution, leaving an oil which solidifies on standing to a light yellow solid. The solid is dissolved in ether where it is treated with ethereal hydrogen chloride to give a salt as a white solid. The solid is recrystallized from isopropyl alcohol to provide white crystals, 2,3-dihydro-1'-benzylspiro[benzofuran-2,4'-piperidine]-hydrochloride, mp 246°-247° C.

Analysis: Calculated for $C_{19}H_{21}NO.HCl$: 72.24%C; 7.03%H; 4.44%N. Found: 71.95%C; 7.06%H; 4.34%N.

EXAMPLE 2

A. A sample of 2-fluorobenzyl chloride is converted to its Grignard reagent as described in Example 1 and is reacted with a sample of N-methyl-4-piperidone to provide 1-methyl-4-(2-fluorobenzyl)-4-piperidinol, mp 93°-95° C., after two recrystallizations.

B. 12.5 g of 1-methyl-4-(2-fluorobenzyl)-4-piperidinol dissolved in 50 ml of dimethylformamide and 20 ml of benzene are added to a stirred suspension at 120° C. of 2.3 g of a 57% oil dispersion of sodium hydride in 110 ml of dimethylformamide and 20 ml of benzene. The reaction mixture is stirred at 120° C. for 84 hours and then successively permitted to cool to ambient temperature, poured into 800 ml of ice-water and extracted with ether. The combined ether extracts were dried before the ether evaporated leaving a light yellow oil. The oil is dissolved in ether and converted to its hydrochloride salt with ethereal hydrogen chloride. The salt is recrystallized twice from an ethanol-ether mixture to provide the product, 2,3-dihydro-1'-methylspiro[benzofuran-2,4'-piperidine]hydrochloride, mp 248°-250° C.

Analysis: Calculated for $C_{13}H_{17}NO.HCl$: 65.13%C; 7.57%H; 5.84%N; 14.79%Cl. Found: 64.92%C; 7.51%H; 5.85%N; 14.92%Cl.

EXAMPLE 3

A. A sample of 2-fluorobenzyl chloride is converted to its Grignard reagent which is reacted with 1-($\beta$-phenethyl)-4-piperidone to provide 1-($\beta$-phenethyl)-4-(2-fluorobenzyl)-4-piperidinol in the manner described in Example 1A. The free base is dissolved in ether where it is treated with ethereal hydrogen chloride to provide the salt, mp 187°-189° C., after two recrystallizations from ethanol.

B. A solution of 34.3 g of 1-($\beta$-phenethyl)-4-(2-fluorobenzyl)-4-piperidinol in 250 ml of dimethylformamide is added to a stirred suspension of 3.2 g of 99% sodium hydride in 250 ml of dimethylformamide. The reaction mixture is stirred at 120° C. for 3 hours, permitted to cool to ambient temperature, and then poured into 750 ml of ice-water. The biphasic mixture is extracted thrice with ether, and the combined ether extracts are dried and then concentrated to a light yellow oil. The oil is dissolved in a small amount of ether where it is converted to its hydrogen chloride salt, a white precipitate. The salt is collected and recrystallized twice from ethanol to provide the product, 2,3-dihydro-1'-($\beta$-phenethyl)spiro[benzofuran-2,4'-piperidine]hydrochloride, mp 270°-272° C.

Analysis: Calculated for $C_{20}H_{23}NO.HCl$: 72.82%C; 7.33%H. 4.24%H; 10.74%Cl. Found: 72.65%C; 7.46%H; 4.18%H; 10.76%Cl.

EXAMPLE 4

A. To a suspension of 3.4 g of magnesium shavings in 50 ml of ether is added a crystal of iodine followed by a few mls of a solution of 20.6 g of 2-fluorobenzyl chloride in 100 ml of ether. Thereafter, the reaction is initiated via a hot air gun before adding dropwise, while maintaining the reaction at reflux, the remaining 2-fluorobenzylchloride-ether solution. After total addition the reaction is maintained at reflux with stirring for an additional hour before successively adding 100 ml of ether and adding dropwise with vigorous stirring a solution of 25.0 g of N-benzyl-3-pyrrolidinone in 100 ml of ether. After complete addition the resulting suspension is refluxed for an additional 2 hours, stirred at ambient temperature for 16 more hours, and then filtered. The filter cake is washed well with ether and then hydrolyzed by stirring in an ice-ammonium chloride solution. The aqueous solution is extracted thrice with ether and the combined ether extracts are washed, successively, with water and a sodium chloride solution and dried. The solvent is removed and the residue is distilled at 135°-140° C., 0.1 mm pressure to provide a viscous yellow oil which solidifies upon standing. The solid is recrystallized twice from an ethanol-water mixture to give the product, 1-benzyl-3-(2-fluorobenzyl)-3-pyrrolidinol, mp 75°-77° C.

B. 38.1 g of 1-benzyl-4-(2-fluorobenzyl)-3-pyrrolidinol dissolved in 125 ml of benzene and 125 ml of dimethylformamide. are added dropwise to a stirring suspension of 4.7 g of sodium hydride in 125 ml benzene and 125 ml of dimethylformamide at 90° C. After total addition the reaction is stirred at 90° C. for 120 hours and then permitted to cool to ambient temperature prior to being poured into 1 l. of ice water. The biphasic mixture is extracted with ether and the combined ether extracts are dried and then evaporated leaving a dark oil. The oil is distilled at 170°–175° C., 0.1 mm pressure, leaving 24 g of a light yellow oil which solidifies on standing. The solid is recrystallized twice from isopropyl alcohol, leaving the product, 2,3-dihydro-1'-benzylspiro[benzofuran-2,3'-pyrrolidine], mp 43°–45° C.

Analysis: Calculated for $C_{18}H_{19}NO$: 81.47%C; 7.22%H; 5.28%N. Found: 81.59%C; 7.39%H; 5.16%N.

EXAMPLE 5

A. A sample of 4-chloro-2-fluorobenzyl bromide is converted to its Grignard reagent which is reacted with N-benzyl-4-piperidone to provide 1-benzyl-4-(4-chloro-2-fluorobenzyl)-4-piperidinol in the manner described in Example 4A. This product is distilled at 175°–180° C., 0.18 mm, to provide an orange oil which is converted in ether to its hydrogen chloride salt. The salt is recrystallized four times from an ethyl alcohol-ether mixture to provide the purified salt, mp 211.5°–213° C.

B. A solution of 8.3 g of 1-benzyl-4-(4-chloro-2-fluorobenzyl)-4-piperidinol in 75 ml of benzene is added dropwise to a stirred suspension at ambient temperature of 1.5 g of sodium hydride (50% oil dispersion) in 100 ml of benzene. After total addition the reaction mixture is brought to reflux before adding 35 ml of dimethylformamide. Thereafter, the reaction mixture, sequentially, is refluxed for 15 minutes, cooled to ambient temperature, and diluted by the dropwise addition of 100 ml of water. The reaction mixture is poured into 1 liter of ice-water and extracted three times with ether. The combined ether extracts are successively washed with a saturated sodium chloride solution, dried and the ether is removed under reduced pressure, leaving an oil. The oil is boiled in hexane and the hexane is removed, leaving a yellow oil which solidifies upon standing. The oil is dissolved in ether where it is converted to its hydrogen chloride salt. The salt is recrystallized thrice from an ethyl alcohol-ether mixture to provide the product, 2,3-dihydro-1'-benzyl-6-chlorospiro[benzofuran-2,4'-piperidine]hydrochloride, mp 257°–259° C.

Analysis: Calculated for $C_{19}H_{20}ClNO \cdot HCl$: 65.15%C; 6.04%H; 4.00%N; 20.24%Cl. Found: 65.01%C; 6.07%H; 4.05%N; 20.11%Cl.

EXAMPLE 6

A. A sample of 5-chloro-2-fluorobenzyl bromide is converted to its Grignard reagent which is reacted with N-benzyl-4-piperidone to provide 1-benzyl-4-(5-chloro-2-fluorobenzyl)-4-piperidinol in the manner described in Example 4A. This product is distilled at 210° C., 0.15 mm, leaving an orange oil. The oil is dissolved in ether where it is converted to its hydrochloride salt which is recrystallized thrice from an ethyl alcohol-ether mixture to provide the product, 1-benzyl-4-(5-chloro-2-fluorobenzyl)-4-piperidinol hydrochloride, mp 217°–219° C.

B. A sample of 1-benzyl-4-(5-chloro-2-fluorobenzyl)-4-piperidinol, free base of A, is treated as described in Example 5B to provide the salt, 2,3-dihydro-1'-benzyl-5-chlorospiro[benzofuran-2,4'-piperidine]hydrochloride.

Analysis: Calculated for $C_{19}H_{20}ClNO \cdot HCl$: 65.15%C; 6.04%H; 4.00%N; 20.24%Cl. Found: 65.21%C; 6.11%H; 3.98%N; 20.06%Cl.

EXAMPLE 7

A solution of 5.3 g of 2,3-dihydro-1'-benzylspiro[benzofuran-2,4'-piperidine], free base of Example 1, in 250 ml of isopropyl alcohol is hydrogenated in a Paar shaker, 50 psig, 65°–70° C., with 1 g of a 10% palladium/carbon catalyst until the uptake of hydrogen is completed. Thereafter, the solution is successively permitted to cool to ambient temperature, filtered and concentrated to dryness, leaving a white solid. The solid is dissolved in a benzene-ether mixture, the solution is filtered through celite and then concentrated again, providing a white solid which, upon trituration with ether, provides the product, 2,3-dihydrospiro[benzofuran-2,4'-piperidine], mp 56°–58.5° C.

Analysis: Calculated for $C_{12}H_{15}NO$: 76.14%C; 8.00%H; 7.40%N. Found: 76.05%C; 8.08%H; 7.27%N.

EXAMPLE 8

A solution of 21.4 g of 2,3-dihydro-1'-benzylspiro[benzofuran-2,3'-pyrrolidine], free base of Example 4, in 200 ml of isopropyl alcohol is hydrogenated with 2.0 g of a 10% palladium on carbon catalyst at 45 psig at 50° C. until the uptake of hydrogen is completed. Thereafter, the reaction mixture is filtered and concentrated under reduced pressure, leaving a yellow oil. The oil is dissolved in ether where it is converted to its hydrogen chloride salt. The salt is recrystallized twice from an ethyl alcohol-ether mixture to provide the product, 2,3-dihydrospiro[benzofuran-2,3'-pyrrolidine]hydrochloride, mp 174°–178° C.

Analysis: Calculated for $C_{11}H_{13}NO \cdot HCl$: 62.23%C; 6.70%H; 6.65%N; 16.83%Cl. Found: 62.17%C; 6.72%H; 6.58%N; 16.60%Cl.

EXAMPLE 9

A stirred solution of 6.1 g of 2,3-dihydro-1'-benzyl-6-chlorospiro[benzofuran-2,4'-piperidine], free base of Example 5, and 2.5 g of ethylchloroformate in 150 ml of benzene is refluxed for 18 hours. Thereafter, the solution is successively permitted to cool to ambient temperature, washed with water, washed with a saturated sodium bicarbonate solution, washed with a saturated sodium chloride solution, dried and concentrated to dryness, leaving 2,3-dihydro-6-chloro-1'-ethoxycarbonylspiro[benzofuran-2,4'-piperidine] as a dark oil. The oil is taken up in a mixture of 50 ml of a 50% potassium hydroxide solution and 100 ml of ethyl alcohol and this mixture is refluxed for 18 hours and then permitted to cool to room temperature before removal of the ethyl alcohol under reduced pressure. The remaining aqueous suspension is extracted with ether and the combined ether extracts are washed with 3 N hydrochloric acid, the acidic wash is basified with 6 N sodium hydroxide and the basified solution is extracted with ether. The combined ether extracts are dried before being concentrated to dryness, leaving on off-white solid. The solid is dissolved in ether where it is converted to its hydrogen chloride salt which is recrystallized twice from ethyl alcohol providing the product, 2,3-dihydro-6-chlorospiro[benzofuran-2,4'-piperidine]hydrochloride, mp 281°–288° C.

Analysis: Calculated for C$_{12}$H$_{14}$ClNO.HCl: 55.40%C; 5.81%H; 5.38%N; 27.26%Cl. Found: 55.21%C; 5.86%H; 5.38%N; 27.07%Cl.

EXAMPLE 10

A sample of 2,3-dihydro-1'-benzyl-5-chlorospiro[benzofuran-2,4'-piperidine], free base of Example 6, is treated in a manner consistent with the procedure of Example 9 to provide the product 2,3-dihydro-5-chlorospiro[benzofuran-2,4'-piperidine]hydrochloride, mp 217°–218° C. This product is obtained after three recrystallizations, two from ethyl alcohol and then one from an ethyl alcohol-ether mixture.

Analysis: Calculated for C$_{12}$H$_{14}$ClNO.HCl: 55.40%C; 5.81%H; 5.38%N; 27.26%Cl. Found: 55.53%C; 5.84%H; 5.40%N; 27.11%Cl.

EXAMPLE 11

3.0 g of allyl bromide are added dropwise to a stirred mixture of 4.0 g of 2,3-dihydrospiro[benzofuran-2,4'-piperidine], Example 7, dissolved in 100 ml of isopropyl alcohol and 13.8 g of potassium carbonate. After total addition, the reaction mixture is maintained at reflux for 6 hours and then stirred at ambient temperature for 48 hours. Thereafter, the reaction mixture is filtered and the filtrate is evaporated to dryness, leaving a light yellow oil. The oil is dissolved in ether where it is converted to its hydrogen chloride salt, a white precipitate. The salt is recrystallized twice from an ethyl alcohol-ether mixture to provide the product, 2,3-dihydro-1'-allylspiro[benzofuran-2,4'-piperidine]hydrochloride, mp 216°–217° C.

Analysis: Calculated for C$_{15}$H$_{19}$NO.HCl: 67.78%C; 7.59%H; 5.27%N; 13.47%Cl. Found: 67.72%C; 7.65%H; 5.18%N; 13.55%Cl.

EXAMPLE 12

1.8 g of cyclopropylcarbonyl chloride are added dropwise to a stirred solution at 0° C. of 3.2 g of 2,3-dihydrospiro[benzofuran-2,4'-piperidine] in 50 ml of pyridine. After total addition the reaction is stirred for 60 hours at ambient temperature and then heated at reflux for 3 hours. Thereafter, the reaction mixture is successively permitted to cool to ambient temperature, poured into 500 ml of water, basified with 20% sodium hydroxide and the solvent is removed under reduced pressure. The residue is triturated with 500 ml of water, extracted twice with ethyl acetate and the combined extracts are dried and the solvent is removed under reduced pressure, leaving a solid. The solid is recrystallized thrice from water to provide white flakes, 2,3-dihydro-1'-cyclopropylcarbonylspiro[benzofuran-2,4'-piperidine], mp 111°–113° C.

Analysis: Calculated for C$_{16}$H$_{19}$NO$_2$: 74.68%C; 7.44%H; 5.44%N. Found: 74.57%C; 7.47%H; 5.39%N.

EXAMPLE 13

A solution of 3.6 g of 4-chlorophenylacetyl chloride in 10 ml of chloroform is added dropwise to a stirred suspension of 3.1 g of 2,3-dihydropsiro[benzofuran-2,4'-piperidine], Example 7, and 7 g of sodium bicarbonate in 40 ml of chloroform. After total addition the reaction mixture is stirred at ambient temperature for 20 hours and then refluxed for 24 hours. Thereafter, the reaction mixture is permitted to cool to ambient temperature and then successively filtered, washed sequentially with 3 N hydrochloric acid, a saturated sodium bicarbonate solution and saturated sodium chloride solution, dried and evaporated, leaving a dark oil. The oil is triturated 4 times with 75 ml of boiling hexane. The combined triturants are collected and permitted to cool, leaving a white precipitate which is collected by filtration. The precipitate is recrystallized thrice from hexane to yield the product 2,3-dihydro-1'-(4-chlorophenylacetyl)-spiro[benzofuran-2,4'-piperidine], mp 108°–110° C.

Analysis: Calculated for C$_{20}$H$_{20}$ClNO$_2$: 70.27%C; 5.90%H; 4.10%N; 10.37%Cl. Found: 70.10%C; 5.94%H; 4.23%N; 10.22%Cl.

EXAMPLE 14

A stirred suspension of 3.5 g of 2,3-dihydrospiro[benzofuran-2,4'-piperidine], Example 7 and 7.5 g of sodium bicarbonate in 40 ml of chloroform are reacted with a solution of 4.4 g of 4-methoxyphenylacetyl chloride in 10 ml of chloroform and thereafter treated according to the procedure of Example 13 to provide a yellow oil. The oil is chromatographed on a silica column with a 3% methyl alcohol in chloroform eluant to provide a white solid which is recrystallized thrice from hexane to provide the product, 2,3-dihydro-1'-[(4-methoxyphenyl)acetyl]spiro[benzofuran-2,4'-piperidine], mp 87°–88° C.

Analysis: Calculated for C$_{21}$H$_{23}$NO$_3$: 74.75%C; 6.87%H; 4.15%N. Found: 74.62%C; 6.96%H; 4.11%N.

EXAMPLE 15

4.0 g of 1-bromo-3-methyl-2-butene in 20 ml of dimethylformamide are added dropwise to a stirred suspension of 5.0 g of 2,3-dihydrospiro[benzofuran-2,4'-piperidine], 10 g of potassium carbonate and a few grams of potassium iodide in 100 ml of anhydrous dimethylformamide. After total addition the reaction mixture is successively refluxed for 2 hours, stirred at ambient temperature for 16 hours, filtered and poured into water. The biphasic mixture is extracted thrice with 150 ml portions of ether, the combined ether extracts are dried and then treated with ethereal hydrochloric acid, effecting a precipitate. The precipitate is collected and recrystallized twice from an ethyl alcohol-ether mixture and then once from ethyl alcohol to provide the product, 2,3-dihydro-1'-(3-methyl-2-butenyl)spiro[benzofuran-2,4'-piperidine]hydrochloride, mp 227°–229° C.

Analysis: Calculated for C$_{17}$H$_{23}$NO.HCl: 60.49%C; 8.23%H; 4.76%N. Found: 69.57%C; 8.25%H; 4.76%N.

EXAMPLE 16

3 ml of acetyl chloride in 10 ml of chloroform are added dropwise to a stirred suspension of 6.0 g of 2,3-dihydrospiro[benzofuran-2,4'-piperidine], Example 7, and 14.0 g of sodium bicarbonate in 75 ml of chloroform. After total addition, the reaction mixture is successively stirred at ambient temperature for 16 hours, filtered, washed sequentially with water, dilute hydrochloric acid and a saturated sodium chloride solution, dried and the solvent is removed under reduced pressure, leaving a residue which solidifies upon standing. The solid is recrystallized twice from hexane to give the product, 2,3-dihydro-1'-acetylspiro[benzofuran-2,4'-piperidine], mp 94°–97° C.

Analysis: Calculated for C$_{14}$H$_{17}$NO$_2$: 72.70%C; 7.41%H; 6.05%N. Found: 72.85%C; 7.47%H; 6.08%N.

EXAMPLE 17

A mixture of 4.2 g of cyclobutylcarbonyl chloride in 10 ml of chloroform is added dropwise to a stirred mixture of 6.0 g of 2,3-dihydrospiro[benzofuran-2,4'- piperidine], Example 7, and 20.0 g of potassium carbonate in 75 ml of chloroform. After total addition, the reaction mixture is successively refluxed for 24 hours, cooled, filtered and poured into water. The biphasic mixture is sequentially washed with 3 N hydrochloric acid, 3 N sodium hydroxide, a saturated sodium chloride solution, dried and the solvent is removed, leaving a solid residue. The residue is recrystallized twice from a benzene-hexane mixture to give the product, 2,3-dihydro-1'-cyclobutylcarbonylspiro[benzofuran-2,4'-piperidine], mp 91°–93° C.

Analysis: Calculated for $C_{17}H_{21}NO_2$: 75.25%C; 7.80%H; 5.16%N. Found: 75.15%C; 7.88%H; 5.14%N.

EXAMPLE 18

A mixture of 4.7 g of ethyl oxalyl chloride in 15 ml of chloroform is added dropwise to a stirred mixture of 5.0 g of 2,3-dihydrospiro[benzofuran-2,4'-piperidine], Example 7, and 10.0 g of sodium bicarbonate in 50 ml of chloroform. After total addition, the reaction mixture is successively refluxed for 3 hours, stirred for 16 hours at ambient temperature, filtered, sequentially washed with water, 3 N hydrochloric acid, saturated sodium bicarbonate solution, saturated sodium chloride solution, dried and the solvent is removed under reduced pressure, leaving a tan solid. The solid is chromatographed through a silica gel column with a 2% methyl alcohol in chloroform eluant to purify the product, which is recrystallized from hexane to give 2,3-dihydro-1'-ethoxyoxalylspiro[benzofuran-2,4'-piperidine], mp 87°–91° C., of the formula

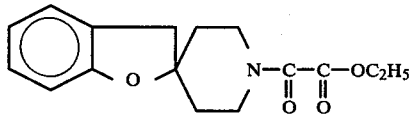

Analysis: Calculated for $C_{16}H_{19}NO_4$: 66.42%C; 6.62%H; 4.84%N. Found: 66.51%C; 6.60%H; 4.84%N.

EXAMPLE 19

A sample of 5.8 g of 2,3-dihydrospiro[benzofuran-2,4'-piperidine], Example 7, is treated with 4.8 g of 2-furoyl chloride according to the procedure of Example 18 to provide an off-white solid. This solid is purified by three recrystallizations from hexane to provide the product, 2,3-dihydro-1'-(2-furoyl)spiro[benzofuran-2,4'-piperidine], mo 102°–103° C.

Analysis: Calculated for $C_{17}H_{17}NO_3$: 72.07%C; 6.05%H; 4.94%N. Found: 72.22%C; 6.10%H; 4.91%N.

EXAMPLE 20

6.0 g of 3-phenoxypropylbromide in 30 ml of dimethylformamide are added dropwise to a stirred mixture of 5.0 g of 2,3-dihydrospiro[benzofuran-2,4'-piperidine], Example 7, 10 g of potassium carbonate, and 1 g of potassium iodide. After total addition, the reaction mixture is successively refluxed for 3 hours, permitted to cool at ambient temperature, filtered and poured into water. The biphasic mixture is extracted with ether and the combined ether extracts are washed with a saturated sodium chloride solution, dried and the solvent is removed, leaving a tan oil. The oil is dissolved in ether where it is converted to its hydrogen chloride salt which is collected and recrystallized twice from ethyl alcohol to provide the product, of 2,3-dihydro-1'-(3-phenoxypropyl)spiro[benzofuran-2,4'-piperidine]hydrochloride, mp 220°–223° C.

Analysis: Calculated for $C_{21}H_{25}NO_2.HCl$: 70.08%C; 7.28%H; 3.89%N. Found: 70.40%C; 7.34%H; 3.82%N.

EXAMPLE 21

A stirred mixture of 5.0 g of 2,3-dihydrospiro[benzofuran-2,4'-piperidine], Example 7, and 15 g of sodium bicarbonate in 75 ml of chloroform is treated with a mixture of 8.8 g of 3,4,5-trimethoxybenzoyl chloride in 125 ml of chloroform according to the procedure of Example 7 to provide a tan solid. The solid is sequentially recrystallized from ethyl alcohol, chromatographed through a silica gel column with a 2% methyl alcohol in chloroform eluant and recrystallized from ethyl alcohol to give the product, 2,3-dihydro-1'-(3,4,5-trimethoxybenzoyl)spiro[benzofuran-2,4'-piperidine], mp 148°–150° C.

Analysis: Calculated for $C_{22}H_{25}NO_5$: 68.91%C; 6.57%H; 3.65%N. Found: 69.01%C; 6.61%H; 3.54%N.

EXAMPLE 22

6.1 g of 1-(indol-3-glyoxylyl)chloride are carefully added portionwise to a stirred mixture of 4.0 g of 2,3-dihydrospiro[benzofuran-2,4'-piperidine], Example 7, in 75 ml of chloroform and 5.0 g of potassium carbonate in 50 ml of water. After total addition, the reaction mixture is stirred at ambient temperature for 24 hours and then the organic and aqueous layers are separated. The aqueous layer is extracted with chloroform and the combined extracts sequentially washed successively with water, 3 N hydrochloric acid and a saturated sodium bicarbonate solution, dried and the solvent removed leaving a solid. The solid is chromatographed through a silica gel column with a 2% methyl alcohol in chloroform eluant and then recrystallized from an ethyl alcohol-water mixture to provide the product 2,3-dihydro-1'-(indol-3-ylglyoxylolyl)spiro[benzofuran-2,4'-piperidine], mp 226°–228° C., having the formula

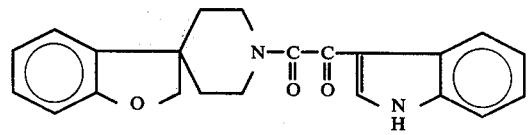

Analysis: Calculated for $C_{22}H_{20}N_2O_3$: 73.32%C; 5.59%H; 7.77%N. Found: 73.31%C; 5.67%H; 7.87%N.

EXAMPLE 23

A solution of 4.0 g of phenylacetyl chloride in 10 ml of chloroform is added dropwise to a stirred solution of 4.0 g of 2,3-dihydrospiro[benzofuran-2,3'-pyrrolidine], free base of Example 8, and 3 ml of triethylamine in 40 ml of chloroform. After total addition, the reaction mixture is stirred successively at ambient temperature for 18 hours and at reflux for 3 hours and then permitted to cool to ambient temperature before being poured into 100 ml of water. The organic layer is collected and then washed sequentially with dilute acid, dilute base, a saturated sodium chloride solution and dried. Thereafter, the solvent is evaporated off, leaving a dark oil which is chromatographed through a silica gel column with a 5% methyl alcohol in chloroform eluant, leaving a light yellow oil. This oil is triturated with boiling hexane, the triturant is decanted and allowed to cool, which causes a precipitate to appear. The precipitate is collected and recrystallized twice from hexane to give the pure product, 2,3-dihydro-1'-(phenylacetyl)spiro[benzofuran-2,3'-pyrrolidine], mp 98°–99° C.

Analysis:
Calculated for $C_{19}H_{19}NO_2$: 77.79%C; 6.53%H; 4.77%N. Found: 77.55%C; 6.72%H; 4.72%N.

EXAMPLE 24

A solution of 3.2 g of 2,3-dihydro-1'-cyclopropylcarbonylspiro[benzofuran-2,3'-piperidine], Example 12, in 75 ml of tetrahydrofuran is added dropwise to a stirred suspension of 0.60 g of lithium aluminum hydride in 50 ml of tetrahydrofuran. After total addition the reaction mixture is refluxed for 4 hours and then stirred for 16 hours at ambient temperature. The excess lithium aluminum hydride is destroyed by the dropwise addition of 75 ml of water before filtering the reaction mixture. The filtrate is successively washed with water and extracted with chloroform. The combined chloroform extracts are dried and evaporated to dryness, leaving a yellow oil which is dissolved in ether where it is converted to its hydrogen chloride salt. The salt is recrystallized twice from an ethyl alcohol-ether mixture to provide the product, 2,3-dihydro-1'-cyclopropylmethylspiro[benzofuran-2,4'-piperidine]hydrochloride, mp 221°–223° C.

Analysis: Calculated for $C_{16}H_{21}NO.HCl$: 68.68%C; 7.93%H; 5.01%N; 12.67%Cl. Found: 68.52%C; 8.03%H; 4.95%N; 12.60%Cl.

EXAMPLE 25

A solution of 10 ml of VITRIDE in 10 ml of benzene is added dropwise to a stirred solution of 4.7 g of 2,3-dihydro-1'-[(4-methoxyphenyl)acetyl]spiro[benzofuran-2,4'-piperidine], Example 14, in 40 ml of benzene. After total addition, the reaction mixture is heated at reflux until the reduction is completed. Thereafter, the mixture is cooled in an ice bath before the dropwise addition of 15 ml of water and then 15 ml of 6 N sodium hydroxide. The aqueous phase is extracted with 150 ml of benzene, the extract is combined with the organic phase and the total organic solution is washed with a saturated sodium chloride solution and then dried. The solvent is evaporated, leaving a light yellow oil which is dissolved in ether where it is converted to its hydrogen chloride salt. The salt is collected by filtration and recrystallized twice from ethyl alcohol and then once from an ethyl alcohol-ether mixture to give the product 2,3-dihydro-1'-(4-methoxy-β-phenethyl)spiro[benzofuran-2,4'-piperidine]hydrochloride, mp 274°–275° C.
Analysis: Calculated for $C_{21}H_{25}NO_2.HCl$: 70.08%C; 7.28%H; 3.89%N; 9.85%Cl. Found: 69.95%C; 7.41%H; 3.96%N; 9.73%Cl.

EXAMPLE 26

A solution of 3.7 g of 2,3-dihydro-1'-(phenylacetyl)spiro[benzofuran-2,3'-pyrrolidine], Example 23, in 30 ml of tetrahydrofuran is added dropwise to a stirred suspension of 0.7 g of lithium aluminum hydride in 40 ml of tetrahydrofuran. After total addition, the reaction mixture is refluxed for 6 hours and then stirred for 18 hours at ambient temperature while 50 ml of water are added dropwise while the reaction mixing is being cooled in an ice-methyl alcohol bath. The reaction mixture is filtered and the filtrate is evaporated to dryness, leaving a yellow oil. The oil is chromatographed through an alumina column with an ether eluant, providing an oil which is dissolved in ether where it is converted to its oxalic acid salt. The salt is collected and recrystallised thrice from ethyl alcohol to provide the product, 2,3-dihydro-1'-(β-phenethyl)spiro[benzofuran-2,3'-pyrrolidine]oxalate, mp 158°–161° C.

Analysis: Calculated for $C_{19}H_{21}NO.(CO_2H)_2$: 68.28%C; 6.28%H; 3.79%N. Found: 68.10%C; 6.43%H; 3.75%N.

EXAMPLE 27

A solution of 3.9 g of 2,3-dihydro-1'-acetylspiro[benzofuran-2,4'-piperidine], Example 16, in 50 ml of tetrahydrofuran is added dropwise to a stirred suspension of 0.7 g of lithium aluminum hydride in 50 ml of tetrahydrofuran. After total addition, the reaction mixture is successively refluxed for 3 hours, stirred for 16 hours at ambient temperature and cooled in an ice-salt bath while 30 ml of water are added dropwise. The reaction is filtered and the filter cake is washed with ether. The ether washings are dried and ethereal-hydrogen chloride is added, effecting a precipitate. The precipitate is collected by filtration and recrystallized twice from an ethyl alcohol-ether mixture to provide the product, 2,3-dihydro-1'-ethylspiro[benzofuran-2,4'-piperidine]hydrochloride, mp 240°–242° C.

Analysis: Calculated for $C_{14}H_{19}NO.HCl$: 66.26%C; 7.94%H; 5.52%N. Found: 66.24%C; 7.97%H; 5.51%N.

EXAMPLE 28

A solution of 7.3 g of 2,3-dihydro-1'-(4-chlorophenylacetyl)spiro[benzofuran-2,4'-piperidine], Example 13, in 100 ml of tetrahydrofuran is added dropwise to a stirred solution, under nitrogen, of 40 ml of 1.08 M diborane in tetrahydrofuran. After total addition, the reaction mixture is successively heated at reflux for 2 hours, stirred for 16 hours at ambient temperature and 30 ml of 6 N hydrochloric acid are added dropwise. Thereafter, the solvent is removed under reduced pressure and the resulting suspension is basified with 2 N sodium hydroxide. The basified mixture is extracted with chloroform and the combined chloroform extracts are dried and then concentrated. The residue is triturated with ether, effecting a precipitate which is recrystallized twice from an ethyl alcohol-water mixture providing white needles, 2,3-dihydro-1'-(4-chloro-β-phenethyl)spiro[benzofuran-2,4'-piperidine], mp 64°–66° C.

Analysis: Calculated for $C_{20}H_{22}ClNO$: 73.27%C; 6.77%H; 4.27%N. Found: 73.16%C; 6.71%H; 4.22%N.

EXAMPLE 29

A solution of 2,3-dihydro-1'-cyclobutylcarbonylspiro[benzofuran-2,4'-piperidine], Example 17, in 75 ml of tetrahydrofuran is added dropwise to a stirred suspension of 1.3 g of lithium aluminum hydride in 75 ml of tetrahydrofuran. After total addition, the reaction mixture is successively refluxed for 2 hours, cooled in an ice bath and 20 ml of water are added dropwise. The reaction is filtered and the filter cake is washed well with ether. The ether washings are combined with the filtrate which is then concentrated under reduced pressure, leaving a pale yellow oil. The oil is dissolved in ether where it is converted to its hydrogen chloride salt. The salt is collected and recrystallized twice from an ethyl alcohol-ether mixture to give the product, 2,3-dihydro-1'-cyclobutylmethylspiro[benzofuran-2,4'-piperidine]hydrochloride, mp 226°–228° C.

Analysis: Calculated for $C_{17}H_{23}NO.HCl$: 69.49%C; 8.23%H; 4.76%N. Found: 69.25%C; 8.12%H; 4.82%N.

EXAMPLE 30

A solution of 5.0 g of 2,3-dihydro-1'-ethyloxalylspiro[benzofuran-2,4'-piperidine], Example 18, in 75 ml of tetrahydrofuran is added dropwise to a stirred suspension under nitrogen of 2.2 g of lithium aluminum hydride in 50 ml of tetrahydrofuran. After total addition, the reaction mixture is successively refluxed for 3 hours, stirred for 16 hours at ambient temperature, cooled in an ice bath and 20 ml of water are added dropwise. The reaction mixture is filtered, the filter cake washed well with ether and the filtrate is dried. The solvent is removed under reduced pressure, leaving a yellow solid. The solid is dissolved in ether where it is converted to its hydrogen chloride salt. The salt is recrystallized from an ethyl alcohol-ether mixture to provide the product, 2,3-dihydro-1'-(β-hydroxyethyl)spiro[benzofuran-2,4'-piperidine]hydrochloride, mp 176°–178° C.

Analysis: Calculated for $C_{14}H_{19}NO_2.HCl$: 62.33%C; 7.47%H; 5.19%N. Found: 62.24%C; 7.56L %H; 5.11%N.

EXAMPLE 31

A solution of 6.5 g of 2,3-dihydro-1'-(2-furoyl)spiro[benzofuran-2,4'-piperidine], Example 19, in 75 ml of tetrahydrofuran is added dropwise to a stirred suspension of 1.1 g of lithium aluminum hydride in 75 ml of tetrahydrofuran. After total addition, the reaction mixture is successively refluxed for 3 hours, stirred at ambient temperature for 16 hours and cooled in an ice bath while 20 ml of water are added dropwise. Thereafter, the mixture is filtered, the filter cake is washed with ether and the filtrate is dried and then evaporated at reduced pressure, leaving a yellow oil. The oil is chromatographed through an alumina column with an ether eluant to provide a milky white oil. This oil is dissolved in ether where it is converted to its oxalic acid salt. The salt is collected and recrystallized twice from ethyl alcohol to provide the product, 2,3-dihydro-1'-furfurylspiro[benzofuran-2,4'-piperidine]oxalate, mp 145°–147° C.

Analysis: Calculated for $C_{17}H_{19}NO_2.(CO_2H)_2$: 63.50%C; 5.89%H; 3.90%N. Found: 63.73%C; 5.89%H; 3.82%N.

EXAMPLE 32

A stirred suspension under nitrogen of 1.5 g of lithium aluminum hydride in 150 ml of tetrahydrofuran is treated with a solution of 2,3-dihydro-1'-(indol-3-ylglyoxyloyl)spiro[benzofuran-2,4'-piperidine], Example 22, in 75 ml of tetrahydrofuran according to the procedure of Example 22 to provide a tan solid. The solid is successively recrystallized from an ethyl alcohol-water mixture, chromatographed through a silica gel column with a 2% methyl alcohol in chloroform eluant and recrystallized from ethyl alcohol to provide the product, 2,3-dihydro-1'-[2-(3-indolyl)ethyl]spiro[benzofuran-2,4'-piperidine], mp 167°–169° C.

Analysis: Calculated for $C_{22}H_{24}N_2O$: 79.48%C; 7.28%H; 8.43%N. Found: 79.38%C; 7.34%H; 8.45%N.

EXAMPLE 33

A stirred suspension under nitrogen of 1.0 g of lithium aluminum hydride in 150 ml of tetrahydrofuran is treated with a solution of 6.0 g of 2,3-dihydro-1'-(3,4,5-trimethoxybenzoyl)spiro[benzofuran-2,4'-piperidine], Example 21, in 50 ml of tetrahydrofuran according to the procedure of Example 27 to provide a light yellow oil. The oil is dissolved in ether where it is converted to its hydrogen chloride salt. The salt is collected and recrystallized twice from an ethyl alcohol-ether mixture to provide the product, 2,3-dihydro-1'-(3,4,5-trimethoxybenzyl)spiro[benzofuran-2,4'-piperidine]hydrochloride, mp 218°–219° C.

Analysis: Calculated for $C_{22}H_{27}NO_4.HCl$: 65.10%C; 6.95%H; 3.45%N. Found: 64.92%C; 7.01%H; 3.42%N.

EXAMPLE 34

3.8 g of nitric acid (sp gr 1.42) in 30 ml of glacial acetic acid are added dropwise to a stirred solution of 4.7 g of 2,3-dihydro-1'-acetylspiro[benzofuran-2,4'-piperidine], Example 16, in 65 ml of glacial acetic acid. After total addition, the reaction mixture is slowly heated to 100° C. over a 2 hour span and then cooled and poured into 500 ml of water. The diluted mixture is extracted with chloroform and the chloroform extracts are washed sequentially with a saturated sodium bicarbonate solution, a saturated sodium chloride solution and then dried. The chloroform is removed under reduced pressure. The residue is triturated with ether, causing an orange precipitate which is collected and recrystallized first from an ethyl alcohol-ether mixture and then from ethyl alcohol to provide the product, 2,3-dihydro-1'-acetyl-5-nitrospiro[benzofuran-2,4'-piperidine], mp 149°–150° C.

Analysis: Calculated for $C_{14}H_{16}N_2O_4$: 60.86%C; 5.84%H; 10.14%N. Found: 60.83%C; 5.82%H; 10.14%N.

EXAMPLE 35

A solution of 3.4 g of 2,3-dihydro-1'-acetyl-5-nitrospiro[benzofuran-2,4'-piperidine] in 150 ml of 6 N hydrochoric acid is refluxed for 45 hours and then stirred at ambient temperature for 16 hours. Thereafter, the reaction mixture is successively extracted once with ether, basified with 6 N sodium hydroxide and extracted thrice with ether. The combined ether extracts are dried and the solvent is removed, leaving a yellow residue. The residue is dissolved in ether where it is converted to its hydrogen chloride salt. The salt is collected, dried and finally recrystallized twice from ethyl alcohol to give the product, 2,3-dihydro-5-nitrospiro[benzofuran-2,4'-piperidine]hydrochloride, mp 265°–266° C.

Analysis: Calculated for $C_{12}H_{14}N_2O_3.HCl$: 53.24%C; 5.59%H; 10.35%N. Found: 53.36%C; 5.77%H; 10.28%N.

We claim:
1. A compound of the formula

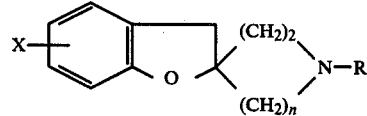

or a pharmaceutically acceptable acid addition salt thereof in which X is hydrogen, nitro, amino, chlorine, fluorine, bromine or methoxy; R is hydrogen, alkyl, alkenyl, hydroxyethyl, alkanoyl, alkoxyoxalyl, unsubstituted or substituted phenylalkanoyl, unsubstituted or substituted benzoyl, unsubstituted or substituted phenylalkyl, cycloalkylalkyl, cycloalkylcarbonyl, furfuryl, furoyl, alkoxycarbonyl, phenoxycarbonyl, unsubstituted or substituted phenoxyalkyl, N-[2-(3-indolyl- )ethyl] or (indol-3-yloxalyl) wherein said alkyl, alkenyl, alkanoyl and alkoxy groups have from 1 to 6 carbon atoms, said cycloalkyl groups have from 3 to 7 carbon atoms and the substituents of said substituted groups are selected from nitro, amino, halogen and methoxy; and n is the integer 1 or 2.

2. A compound defined in claim 1 in which R is hydrogen or benzyl.

3. A compound defined in claim 2 in which n is 2.

4. A compound defined in claim 1 in which R is alkyl, alkenyl, hydroxyethyl, alkanoyl, unsubstituted or substituted phenylalkanoyl, unsubstituted or substituted benzoyl, unsubstituted or substituted phenylalkyl, cycloalkylalkyl, cycloalkylcarbonyl, furfuryl, furoyl, alkoxycarbonyl, phenoxycarbonyl, unsubstituted or substituted phenoxyalkyl, N-[2-(3-indolyl)ethyl] or (indol-3-yloxalyl).

5. A compound defined in claim 4 in which R is alkyl of between 1 and 3 carbon atoms; alkenyl of between 2 and 4 carbon atoms; hydroxyethyl; alkanoyl of between 2 and 4 carbon atoms; unsubstituted or substituted phenylacetyl; benzyl, unsubstituted or substituted phenylethyl, cycloalkylmethyl, cycloalkylcarbonyl, furfuryl, furoyl, ethoxycarbonyl, phenoxycarbonyl or unsubstituted or substituted phenoxyalkyl in which the alkyl portion contains between 1 and 4 carbon atoms.

6. A compound defined in claim 5 in which n is 2.

7. A compound defined in claim 5 in which n is 1.

8. A compound defined in claim 4 in which R is N-[2-(3-indolyl)ethyl] or N-(indol-3-yloxalyl).

9. A compound defined in claim 8 in which n is 2.

10. The compound defined in claim 1 which is 2,3-dihydro-1'-methylspiro[benzofuran-2,4'-piperidine] or a pharmaceutically acceptable acid addition salt thereof.

11. The compound defined in claim 1 which is 2,3-dihydro-1'-cyclobutylmethylspiro[benzofuran-2,4'-piperidine] or a pharmaceutically acceptable acid addition salt thereof.

12. The compound defined in claim 1 which is 2,3-dihydro-1-(β-phenethyl)spiro[benzofuran-2,4'-piperidine] or a pharmaceutically acceptable acid addition salt thereof.

13. The compound defined in claim 1 which is 2,3-dihydro-1'-(β-phenethyl)spiro[benzofuran-2,3'-pyrrolidine] or a pharmaceutically acceptable acid addition salt thereof.

14. The compound defined in claim 1 which is 2,3-dihydro-5-nitrospiro[benzofuran-2,4'-piperidine] or a pharmaceutically acceptable acid addition salt thereof.

15. The compound defined in claim 1 which is 2,3-dihydrospiro[benzofuran-2,4'-piperidine] or a pharmaceutically acceptable acid addition salt thereof.

16. The compound defined in claim 1 which is 2,3-dihydrospiro[benzofuran-2,3'-pyrrolidine]hydrochloride or a pharmaceutically acceptable acid addition salt thereof.

17. The compound defined in claim 1 which is 2,3-dihydro-6-chlorospiro[benzofuran-2,4'-piperidine]hydrochloride or a pharmaceutically acceptable acid addition salt thereof.

18. The compound defined in claim 1 which is 2,3-dihydro-5-chlorospiro[benzofuran-2,4'-piperidine]hydrochloride or a pharmaceutically acceptable acid addition salt thereof.

19. A method of alleviating pain in a patient which comprises administering to a patient an analgesically effective amount of a compound defined in claim 1.

20. A method of tranquilizing a patient which comprises administering to the patient an effective tranquilizing amount of a compound defined in claim 1.

21. An analgesic or tranquilizer composition comprising between 0.5 and 70% by weight of a compound defined in claim 1 and a pharmaceutically acceptable carrier therefor.

22. The method as defined in claim 19 wherein said amount of said compound is from 0.05 to 300 mg/kg of body weight per day.

23. The method as defined in claim 20 wherein said amount of said compound is from 0.05 to 300 mg/kg of body weight per day.

* * * * *

UNITED STATES PATENT AND TRADEMARK OFFICE
CERTIFICATE OF CORRECTION

PATENT NO. : 4,166,119
DATED : August 28, 1979
INVENTOR(S) : Effland et al.

It is certified that error appears in the above-identified patent and that said Letters Patent are hereby corrected as shown below:

Column 1, line 7, "...zofuranpiperidine" should be

--...zofuran-piperidine--;

Column 8, line 4, "were" should be --are--;

line 40, "4.24%H" should be --4.24%N--;

line 41, "4.18%H" should be --4.18%N--;

Column 13, line 50, "mo" should be --mp--;

Column 15, line 63, "mixing" should be --mixture--;

Column 17, line 21, "7.56L %H" should be --7.56%H--.

Signed and Sealed this

Twenty-ninth Day of April 1980

[SEAL]

Attest:

SIDNEY A. DIAMOND

Attesting Officer       Commissioner of Patents and Trademarks